United States Patent [19]

Vandenbossche et al.

[11] 4,238,297

[45] Dec. 9, 1980

[54] PROCESS FOR THE DETERMINATION OF THE CONTENT OF SOLID, DISSOLVED AND WITH WATER IMMISCIBLE ORGANIC SUBSTANCES IN WATER

[75] Inventors: Christiaan Vandenbossche, Zwijnaarde; Laurent Danneels, Varsenare; Jacky Vanhumbeeck, Brugge, all of Belgium

[73] Assignee: Siemen Aktiengesellschaft, Berlin & Munich, Fed. Rep. of Germany

[21] Appl. No.: 2,536

[22] Filed: Jan. 11, 1979

[30] Foreign Application Priority Data

Feb. 1, 1978 [DE] Fed. Rep. of Germany ....... 2804267

[51] Int. Cl.$^3$ ........................................... G01N 27/42
[52] U.S. Cl. ................................ 204/1 T; 23/230 M; 204/195 T
[58] Field of Search ................. 204/1 M, 1 T, 195 T; 23/230 M

[56] References Cited

U.S. PATENT DOCUMENTS 3,726,778  4/1973  Levy et al. ...................... 204/195 T

OTHER PUBLICATIONS

R. Wagner, Vom Wasser, 46, pp. 139–160, 1976.

*Primary Examiner*—G. L. Kaplan
*Attorney, Agent, or Firm*—Hill, Van Santen, Steadman, Chiara & Simpson

[57] ABSTRACT

An automated analysis process and apparatus for analyzing the amount of dispersed water-immiscible solid organic substances in sewage water whereby a precise sample of sewage is taken from a sewage source, admixed with various reagent solutions, including a $K_2Cr_2O_7$—solution under heat-time conditions so that a reaction occurs between the sewage and the reagent and all of the organic substance in the sample are oxidized while simultaneously at least some $Cr^{+6}$—ions are reduced to $Cr^{+3}$—ions. During this oxidation-reduction reaction and at a location remote therefrom, a precise amount of $Fe^{+2}$—ions is generated within an aqueous acidic $Fe^{+3}$—ion containing solution via a coulometric reduction process. Thereafter, the reacted sewage-reagent solution is admixed and reacted with the so-generated $Fe^{+2}$, $Fe^{+3}$—ion containing solution so that any residual $Cr^{+6}$—ions in the sewage-reagent solution are reduced to $Cr^{+3}$—ions and at least some $Fe^{+2}$—ions remain. By biamperometrically titrating the resultant $Fe^{+2}$—ion containing solution with a standardized $Cr^{+6}$—ion containing solution, the precise amount of $Fe^{+2}$—ions within the titrated solution is determined and this provides an indirect indication of the amount of organic substances within the sewage sample. Pneumatic, hydraulic and electrical circuits actuate the various steps and are themselves actuated and controlled by a master control means, such as preprogrammed computer means, which also computationally integrates data from the overall process and automatically determines the amount of organic substances in the samples under analysis.

4 Claims, 4 Drawing Figures

Fig. 2

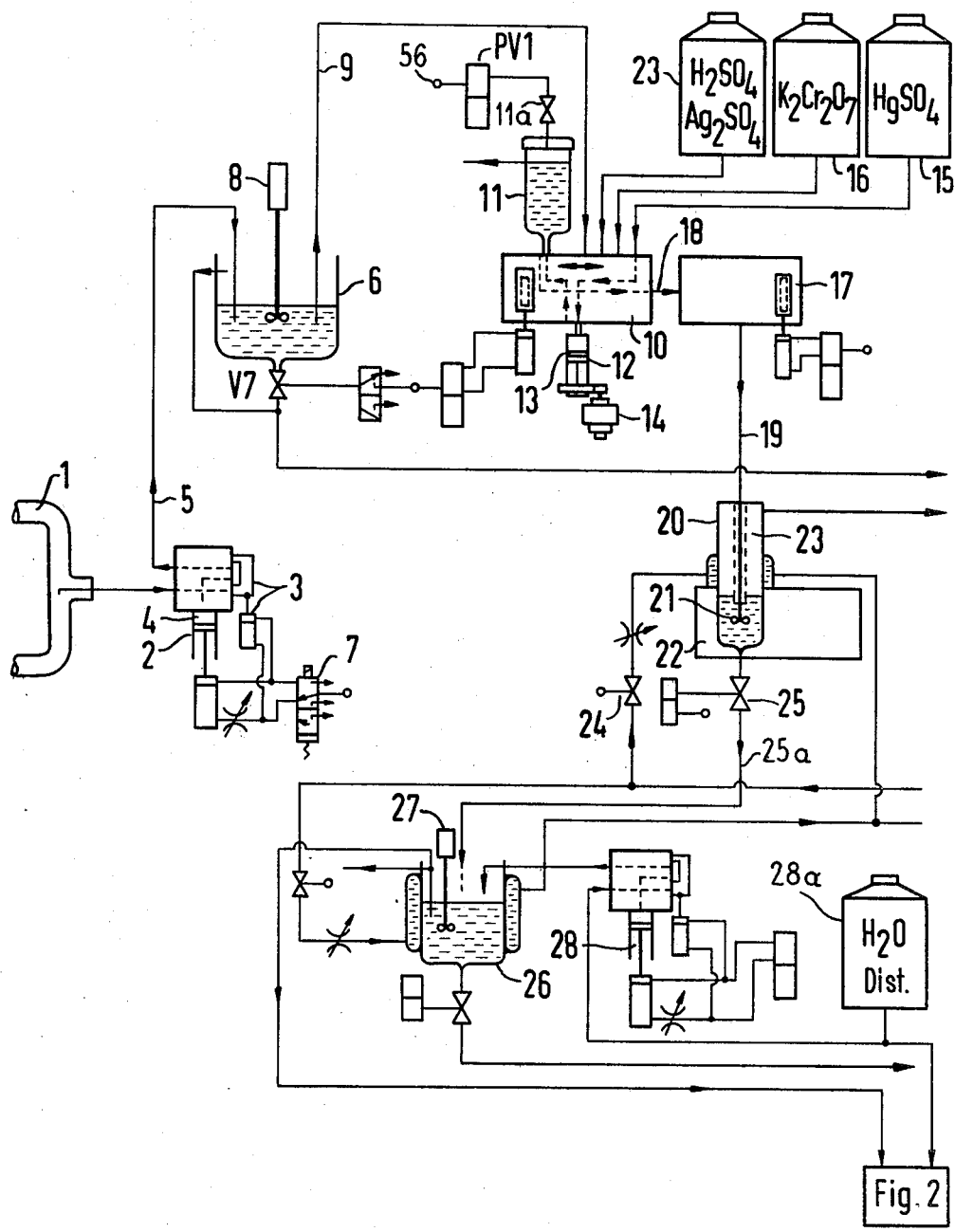

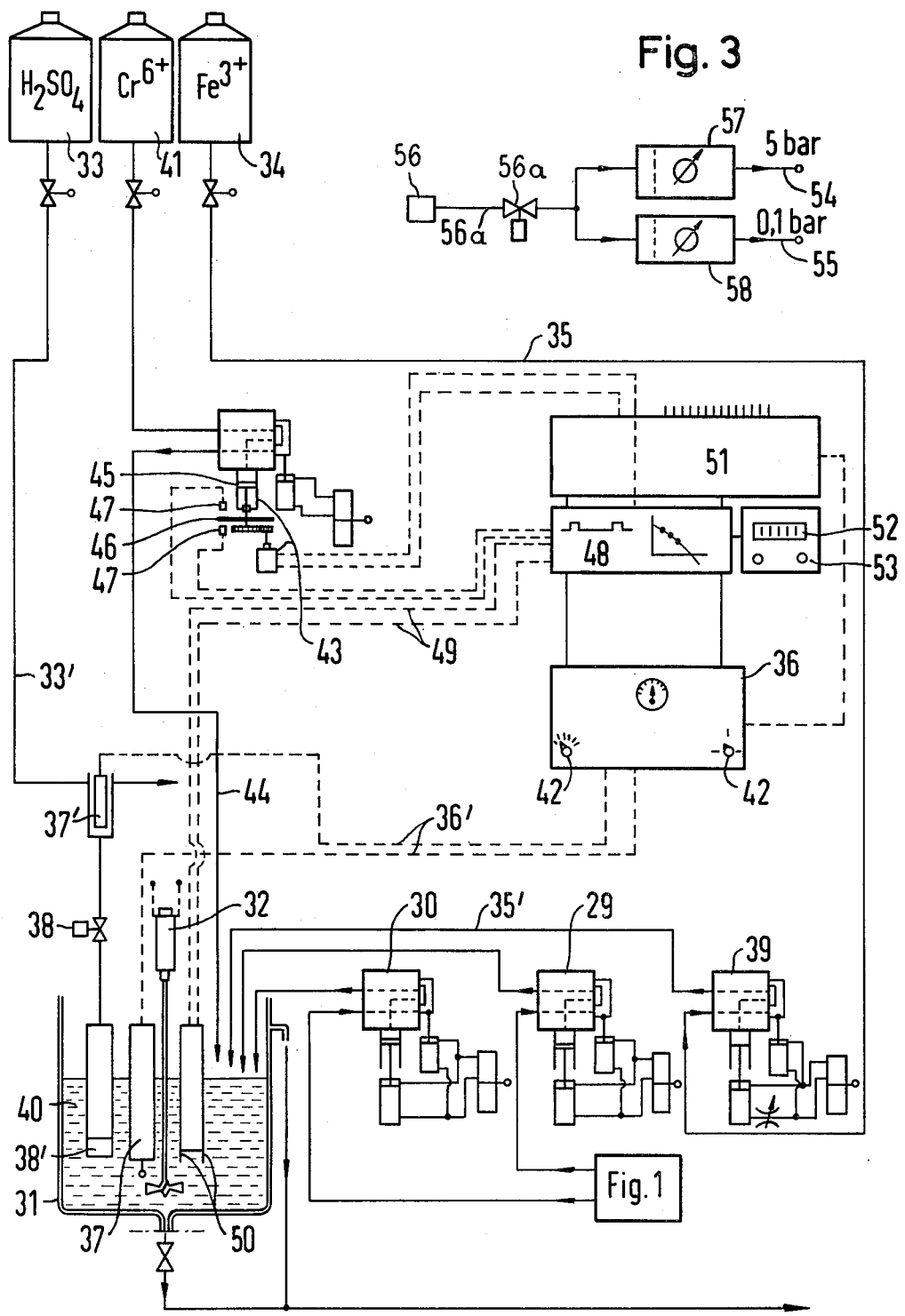

PROCESS FOR THE DETERMINATION OF THE CONTENT OF SOLID, DISSOLVED AND WITH WATER IMMISCIBLE ORGANIC SUBSTANCES IN WATER

BACKGROUND OF THE INVENTION

1. Field of the Invention

The invention relates to the process and apparatus for determining the amount of dispersed water-immiscible solid organic substances in sewage water and somewhat more particularly to a computer-controlled analysis system for accomplishing the foregoing.

2. Prior Art

Analysis of the amount of organic substances contained or dispersed in sewage water or the like is useful for determining the parameters needed for purification or other treatment of such water as well as in determining, for example, the efficiency of the overall sewage system. However, such analysis is rather costly because of the multitude of process steps and individual operation required in accomplishing such analysis. In a typical prior art process, a technician obtains a defined amount of sewage water from a given source thereof, admixes such water with precise amounts of various reagent solutions, including sulfuric acid and silver sulfate to prepare the sewage sample suitable for analysis of the quantity of organic substance therein. Next, the technician admixes the prepared sewage sample with a potassium dichromate, ($K_2Cr_2O_7$), solution and heats the resultant solution close to the boiling point thereof for a period of time sufficient for the oxygen, released from the potassium dichromate solution during the reduction of $Cr^{+6}$-ions into $Cr^{+3}$-ions, to completely oxidize the organic substance. Then the technician determines the residual amount of $Cr^{+6}$-ions in the resultant solution by titrating with a $Fe^{+2}$-ion containing solution so that a reaction in accordance with the following formula scheme takes place:

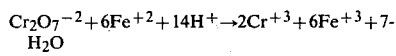

$$Cr_2O_7^{-2} + 6Fe^{+2} + 14H^+ \rightarrow 2Cr^{+3} + 6Fe^{+3} + 7H_2O$$

The technician then notes the amount of consumed $Fe^{+2}$-ion containing solution and converts such indirect measure into the amount of organic substance contained in the sewage sample. The foregoing procedure can only be practically carried out in a laboratory setup wherein a given water or sewage sample defined in terms of its volume, must first be subjected to a pretreatment to prepare it for an orderly analysis. As is known, a wide variety of substances can be found in water or sewage which interfere with an orderly analysis of organic materials therein in accordance with the above described, analytical procedure. Thus, chlorides typically present in water interfere with the above described analysis. In order to mask the free chlorine ions contained in sewage water or the like, a mercury sulfuric acid solution is intimately admixed with the sewage sample before such sample is subjected to analysis. Even in a potassium dichromate solution used as an oxidizing reagent wherein chromium exists as a $6^+$-valent ion, in combination with the distilled water, there is a tendency toward reduction of chromium to a $3^+$-valent ion and this fact must be taken into account during the aforesaid analysis. Further, the $Fe^{+2}$-ion containing solution used for titrating the reacted sewage-reagent solution, is not chemically very stable because the $Fe^{+2}$-ions endeavor to transform themselves into the more stable $Fe^{+3}$-ions. It is therefore necessary for the analytical technician to precisely determine the amount of $Fe^{+2}$-ions in the titration solution which, incidentally, also contains $Fe^{+3}$-ions therein, before beginning the titration procedure. In addition, titrating the reacted sewage-reactant solution with this iron solution is difficult as the end point of the titration, i.e., that point at which all of the $Cr^{+6}$-ions still present in the reacted sewage-reagent solution are reduced to $Cr^{+3}$-ions, is only imprecisely determinable with traditional techinques.

The aforementioned problems do not allow this analysis procedure to be materially accelerated or to be automated, which would be highly desirable.

SUMMARY OF THE INVENTION

The invention provides an automated process and apparatus for determining the amount of water-immiscible solid organic substance within a water source, such as a sewage water source.

In accordance with the principles of the invention, a select water sample is automatically taken and prepared for analysis and reacted with various reagent solutions, including a $K_2Cr_2O_7$-solution in accordance with the afore-described known analysis scheme while substantially simultaneously a required amount of $Fe^{+2}$-ions for titration in accordance with this analysis scheme is automatically generated by coulometric reduction in a $Fe^{+3}$-ion containing solution. Thereafter, the reacted water-reagent sample is automatically admixed with the $Fe^{+2}$-ion containing solution and is titrated with a standardized $Cr^{+6}$-ion containing solution so as to amperometrically determine the precise amount of $Fe^{+2}$-ions within the titrated solution and thus indirectly determine the amount of organic substances within the water sample.

By performing the coulmetric reduction of the $Fe^{+3}$-ion containing solution during the preparation of the water sample for analysis or during the reaction of the sample with the reagents, it is possible to generate an exactly calculated amount of $Fe^{+2}$-ions in and from the $Fe^{+3}$-ion containing solution within a defined time period. Since such $Fe^{+2}$-ion containing solution generated in this manner is immediately utilized as a titrating agent, a prior determination of the $Fe^{+2}$-ion content in the titrating solution, before the actual titration, is no longer required. This innovation, in accordance with the principles of the invention, allows the aforesaid analysis procedure to become automated.

In a preferred embodiment of the invention, the generated amount of $Fe^{+2}$-ions within the $Fe^{+3}$-ion solution is maintained in excess of the maximum amount of possible residual $Cr^{+6}$-ions that may be expected in a reacted water sample-reagent solution. As a result, substantially all $Cr^{+6}$-ions present in such reacted water sample-reagent solution and admixed with the $Fe^{+2}$-ion containing solution are reduced to $Cr^{+3}$-ions and an excess residue of $Fe^{+2}$-ions remain in such mixture. With a "biamperometric titration" of this mixture with a standardized $Cr^{+6}$-ion containing solution, and thus via readily attainable measurement techniques, the residual amount of $Fe^{+2}$-ions in this mixture is readily and accurately determined.

In accordance with the principles of the invention, a precise and automatic measurement of the residual amount of $Cr^{+6}$-ions in the reacted water-reagent solution is attained. Biamperometric titration allows a computationally attainable determination, almost up to the end point of the titration reaction. It is, therefore, preferable to determine the amount of $Fe^{+2}$-ions in the reaction solution by titrating the same with a $Cr^{+6}$-ion containing solution, rather than vice-versa as in the prior art.

In accordance with an apparatus embodiment of the invention, an automated analysis system for carrying out the above-described analysis scheme comprises, in combination, (a) a water sample extraction means including a piston burette connected with a water source; (b) a reagent solution addition means connected to said sample extraction means and including a multi-path metering valve and a collection chamber connected to said metering valve and to reagent solution supply sources as well as to the piston burette; (c) a reactor means connected to the addition means and including a temperature-conrollable chamber, and a fluid-flow line connecting the multi-path metering valve with the reactor means; and (d) a reduction-analysis means connected to said reactor means and including a reduction container and an analysis container, a coulometer connected to the reduction chamber via reduction electrodes, an amperometer connected to the analysis container via measurement electrodes, a computer means connected to the reduction and measurement electrodes and a titration means connected with the analysis chamber and with the computer means, which is also connected with means (a), (b) and (c) for controlling all such means in accordance with a select program.

In such an apparatus system, a coulometer is operationally connected to a controllable electric current source and to reduction electrodes in communication with a $Fe^{+3}$-ion containing solution within the reduction container. The titration means includes a burette means having an axially and rotatably moveable piston or cylinder and an apertured or slotted disk which, upon movement or stroke of the burette piston, delivers a signal to the computer means via a pulse emitter operationally coupled with such disk. Since the computer is also electrically connected with the analysis container via measurement electrodes, the computer means accurately determines the amount of titration fluid passing through the piston burette into the analysis chamber and readily determines the amount of titration fluid utilized and, at the end point, shuts off the burette.

By means of such an apparatus system, the inventive method for determining organic contaminants in a water source can be readily and automatically accomplished. In a suitable reduction container or chamber, $Fe^{+2}$-ions, in a defined amount, are generated via a coulometric reduction of a $Fe^{+3}$-ion containing solution. Preferably, such container or chamber also functions as an analysis container or chamber. The titration burette is provided with an apertured or slotted disk, which upon activation of the burette piston or cylinder delivers a signal to a computer means via a pulse emitter associated with such disk so that the amount of titration solution fed into the analysis chamber by the burette can be accurately determined. The computer means integrates these signals, which are proportional to the amount of titration solution, i.e., $Cr^{+6}$-ion containing solution, supplied to the analysis chamber. For each measured volume of titration fluid, the computer receives a measured current value specific for the volume of titration solution added via the measuring electrodes in the analysis container. When such measured current value falls below a specific magnitude (which is still above a predetermined threshold value), then the computer deactivates the titrator, i.e., the burette, and the computer now computationally determines, with high precision, the exact end or neutral point of the titrated solution.

In accordance with the principles of the invention, the amount of $Fe^{+2}$-ions generated and maintained in the $Fe^{+3}$-ion containing solution is in excess of the expected amount of residual $Cr^{+6}$-ions in the reacted water sample-reagent solution. Subsequent mixing of such reacted water sample-reagent solution with the foregoing iron solution causes all $Cr^{+6}$-ions to be reduced to $Cr^{+3}$-ions and biamperometric titration of the resultant mixture with a standardized $Cr^{+6}$-ion containing solution provides an accurate determination of the residual amount of $Fe^{+2}$-ions in such mixture. In biamperometric titration, a computer means is supplied with a measured current value at constant time interval from the titrated mixture so that when the measured current value falls below a preselected threshold value, the computer means terminates the titration and substantially simultaneously determines the neutral point by extrapolation and displays the resultant data.

BRIEF DESCRIPTION OF THE DRAWINGS

Other objects, features and advantages of the present invention will be appearent from the following description of certain preferred embodiments thereof, taken in conjunction with the accompanying drawings which, by way of illustration, show preferred embodiment of the present invention and the principles thereof and what is now considered to be the best mode contemplated for applying these principles. Other embodiments of the invention, embodying the same or equivalent principles may be used and structural or other changes may be made as desired by those skilled in the art without departing from the spirt and scope of the novel concepts of the invention, and in which:

FIG. 1 is a partial schematic illustration of a first portion of an overall analysis system constructed and operating in accordance with the principles of the invention;

FIG. 2 is a partial schematic illustration of a second portion of an overall analysis system constructed and operating in accordance with the principles of the invention;

FIG. 3 is a partial schematic illustration of a pneumatic circuit utilized in the practice of the invention.

DESCRIPTION OF PREFERRED EMBODIMENT

Figure 4:
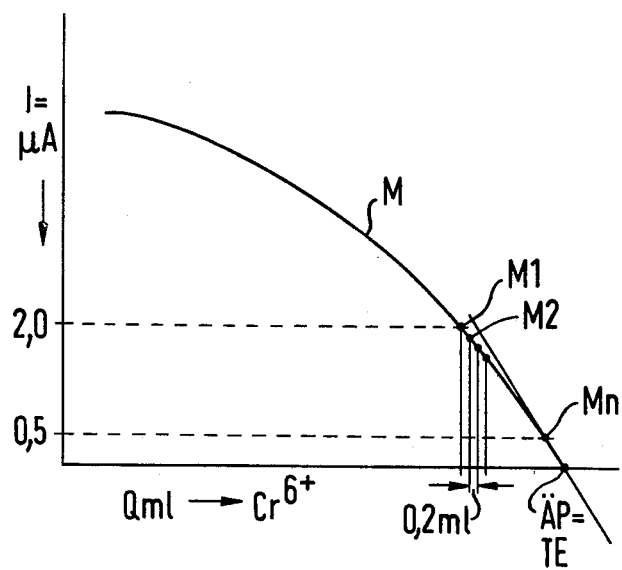
FIG. 4 is a graphical illustration showing the relation between current strength and the amount of $Cr^{+6}$-ions and utilized in the practice of the invention for determining the end point of the analysis procedure.

As shown in FIG. 1, the analysis system of the invention includes a water sample extraction means which is operationally connected with a water circulation source 1, for example, a sewage water line. Such sample extraction means includes an automatically actuated metering syringe means 2. As is known, a reciprocally sliding valve 3 is connected with the metering syringe so that the piston or cylinder space 4 of the syringe is filled with a precisely defined amount of water in one position of the sliding valve and in the other position of the valve, the extracted water sample is ejected from such space via line 5 into a sample mixing container 6. A control means 7 is operationally connected to the metering syringe and to a master process control means (described in conjunction with FIG. 2) so as to regulate the sample extraction in a desired manner. In an exemplary embodiment, the control means 7 is programmed to actuate the metering syringe means 2 so that a 2 ml. sample of raw water is extracted every 30 seconds from the water circulation source 1. The sample mixture container 6 may be of any size desired and in the exemplary embodiment is of a size sufficient to contain a volume of 50 ml. so that with an extraction stroke of the metering syringe having a volume of 2 ml., the sample mixing container is filled with a required amount of raw water in about 13 minutes. This raw water sample is thoroughly mixed by an agitator means 8 operationally associated with the sample mixing container 6 and the master process control means.

After the raw water sample is thoroughly mixed, a select volume thereof is fed to a reagent addition means. Such reagent addition means includes a collection container 11 and a multi-path metering valve means 10. As shown, a fluid feed line 9 provides communication between the sample mixing container 6 and the multi-path metering valve means 10. A burette means 12 having a piston or cylinder 13, whose stroke is adjustable via a threaded rod (not shown) coupled with a reversable motor means 14, which is controllable via the master process control means is connected to the metering valve means 10. In an exemplary embodiment, a 5 ml. sample of mixed raw water is withdrawn via line 9 and the multi-path metering valve means 10 and supplied to the collection container 11 by activation and adjustment of the burette means 12. A plurality of select reagent solution sources 15, 16 and 23 are each provided with fluid feed lines in communication with the multi-path metering valve means 10, further details of which are disclosed and claimed in copending application U.S. Ser. No. 004,372, which is incorporated herein by reference. Depending upon the active path or position of the multi-path metering valve means 10 as well as the position of the piston 13 of burette means 12, specific amounts of select reagent solutions are sucessively fed into the collecting container 11 for admixture with the water sample therein. Thus, in the exemplary embodiment, after a 5 ml. raw water sample is fed into the collecting container 11, various reagent solutions are fed into such container, namely, 0.5 ml. of a mercury sulfate solution from a source 15 thereof for masking free chlorine ions that may be present and 2.5 ml. of an oxidation solution, preferably a potassium dichromate solution, from a source 16 thereof. A second multi-path metering valve means 17 (essentially similar to the multi-path metering valve means 10) is operationally connected to the first multi-path metering valve means 10 via line 18 and to a heatable container 20 via line 19. A select amount, in the exemplary embodiment, about 7.5 ml., of a reagent solution comprised of a mixture of sulfuric acid and silver sulfate is withdrawn from a source 23 thereof via valve means 10 and burette means 12 and fed, via valve means 17 to the container 20. The silver sulfate functions as a catalyst and thus, as a reaction accelerator. This reagent solution may be preheated within container 20.

Next, a compressed gas source 56 is activated by the master process control means to provide a gas pressure P of about 0.1 bar via a pressure valve PV1 and this pressurized gas is fed, via valve means 11a, into collecting container 11 for pneumatically driving the water sample-reagent solution mixture therein through both multi-path valve means 10 and 17, through line 19 and into the container 20. In this manner, the collecting container 11 is emptied and the complete water sample-reagent solution mixture is positioned in container 20, which comprises a reactor means.

The reactor means is thus operational coupled with the reagent addition means and includes a temperature-controllable reactor container 20 and supply line 19 connected with the multi-path metering valve means 17. The reactor container 20 may be provided with an operational agitator means 21 for thoroughly mixing the water sample with the reagent solutions. A thermostatically controlled heating bath means 22 operationally surrounds reactor container 20 so as to heat the contents thereof to a desired temperature. In the exemplary embodiment, the heating bath means 22 is activated so as to heat the water sample-reagent solution mixture to a temperature close to the boiling point of such mixture, i.e., up to about 160° C. The heating bath maintains this elevated temperature for a period of time sufficient for the materials within the reactor container to react. In the exemplary embodiment, this elevated temperature is maintained for at least about 20 minutes. Under such time-temperature conditions, the organic materials in the water sample are oxidized, mostly into water and carbon dioxide, in accordance with the following reaction formula:

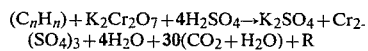

wherein $C_nH_n$ is in the organic material and R is the residue of the oxidation agent $K_2Cr_2O_7$ not consumed during such reaction. Since an excess amount of potassuim dichromate (i.e., excess of the amount estimated to be required for a complete oxidation of organic materials in the raw water sample), is provided in the reaction mixture, a residual amount of $K_2Cr_2O_7$ is present in the spent or reacted mixture, along with a number of other by-product components, such as, for example, $SO_2$, and the reaction products mentioned above. The $Cr^{+6}$-ions contained in the residual potassuim dichromate solution are the components to be determined since this supplies information concerning the amount of organic materials, i.e., the $(C_nH_n)$ wherein n is a positive number, contained in the water sample under analysis.

As can be seen, the reactor means includes, in addition to the container and the bath means, a reflux condensor 23 for any vapors formed during the reaction. Further details of such reactor means are more fully described and claimed in copending application U.S. Ser. No. 004,372, which is incorporated herein by reference. A heat-exchange fluid, such as water, is circulated through a hydraulic circuit about the reflux condensor upon automatic activation of valve means 24 by the master process control means so as to maintain the reflux condensor at a select temperature. After the oxidation-reduction reaction between the water sample and the reagent solution has been completed, the spent reaction mixture is drained from the reactor container into a collecting container 26 via a fluid line 25a having an automatically actuatable valve means 25 therein, which is operationally coupled with the master process control means.

The collecting container 26 is provided, prior to receiving the spent reaction mixture therein, an amount of distilled water from a source 28a thereof via a metering pump means 28. In the exemplary embodiment, the pump means 28 is activated for two strokes thereof so that about 40 ml. of distilled water are provided within container 26. The spent reaction mixture is thus somewhat diluted and is further cooled by a heat-exchange fluid circulating about the exterior of container 26, as schematically illustrated. The so-diluted reaction mixture may be thoroughly mixed with an agitator means 27 operationally associated with the container 26 and the master process control means.

Substantially simultaneously with the preparation of the water sample for analysis and with the oxidation-reduction reaction of such sample with the reagent solutions in the reactor means, a select amount, in the exemplary embodiment about 3 ml., of a sulfuric ammonium ferric sulfate solution from a source 34 thereof is withdrawn via a piston syringe means 39 and fed into an analysis container 31. Similarly, an amount of the distilled water, in the exemplary embodiment about 30 ml., is withdrawn from the distilled water source 28a and admixed with the $Fe^{+3}$-ion containing solution within analysis container 31 via an agitator means 32 operationally associated with container 31 and the master process control means. Thereafter, a precisely defined amount of $Fe^{+2}$-ions estimated to be required for the analysis of residual $Cr^{+6}$-ions in the spent reaction mixture are generated from the so-prepared $Fe^{+3}$-ion containing solution. Such ion reduction is accomplished via a coulometer means 36, which, as is schematically shown, is galvanically connected via electrical lines 36' with a Pt-cathode positioned in contact with the $Fe^{+3}$-ion containing solution 40 in container 31 and with an anode 37' which is separated from the solution 40 in container 31 by a semipermeable membrane 38'. A source 33 containing dilute sulfuric acid, which in the exemplary embodiment is a 25% sulfuric acid solution, is connected via fluid feed line 33' to the anode 37' and selectively connected to the semipermeable membrane 38' via a magnetically actuated valve means 38 in the line between the anode and the solution 40 in container 31. The diluted sulfuric acid solution penetrates the membrane 38 at a specific speed so that any $Fe^{+2}$-ions formed in container 31 cannot diffuse to the anode. By select adjustment, via control knobs 42, 42, of electrical current magnitudes and operating time periods of the coulometer means 36, a reduction current is generated sufficient to produce the precisely desired amount of $Fe^{+2}$-ions within solution 40 in container 31. Upon attainment of the desired amount of $Fe^{+2}$-ions, the reduction current is suppressed by properly adjusting the coulometer means and the connection between the anode 37' and the membrane 38' is interrupted by closing valve means 38 in accordance with a command from the master process control means.

After the spent water sample-reagent solution mixture in container 26 has been suitably diluted, mixed and cooled, a defined amount of such reacted mixture (in the exemplary embodiment, an 8 ml. portion) is withdrawn from container 26 via a piston syringe means 29 and fed into the analysis container 31. Substantially simultaneously, a defined amount of the distilled water (in the exemplary embodiment, two 20 ml. portions) is withdrawn from the distilled water source 28a via a piston syringe means 30 and also fed into the analysis container 31. After these fluid amounts have been fed into the container 31, the resultant solution is throughly admixed via an agitator means 32 operationally associated with container 31 and connected to the master process control means. As explained earlier, the amount of $Fe^{+2}$-ions generated within the $Fe^{+3}$-ion containing solution is in excess of the expected amount of residual $Cr^{+6}$-ions in the reacted water sample-reagent solution mixture. Accordingly, upon admixing of this reacted solution mixture with the $Fe^{+2}$-$Fe^{+3}$-ion containing solution in container 31, all of the $Cr^{+6}$-ions are reduced to $Cr^{+3}$-ions and an excess of $Fe^{+2}$-ions remains therein. The originally generated amount of $Fe^{+2}$-ions is a known quantity and the residual amount of $Fe^{+2}$-ions is measurable so that the amount of $Cr^{+6}$-ions contained in solution 40 of container 31 corresponds to the difference between these $Fe^{+2}$-ion amounts.

In order to accurately and automatically determine the residual amount of $Fe^{+2}$-ions within solution 40 after admixture of the $Fe^{+2}$-,$Fe^{-3}$-ion containing solution with the reacted solution mixture, biamperometric titration is undertaken with a standardized $Cr^{+6}$-ion containing solution. A source 41 for such standardized $Cr^{+6}$-ion containing solution is connected, via a valve-controlled fluid line, with a burette means 43 so that an exactly metered amount of the $Cr^{+6}$-ion containing solution can be controllably fed to the analysis container 31 via fluid line 44. The burette means 43 includes a spindle piston 45 (i.e., an axially moveable piston head connected to a rotatably shaft) operationally associated with an apertured or slotted disk 46 so that the piston and disk move in a coordinated manner. A light source 47 is operationally associated with the disk 46 so that the light beam from source 47 is interrupted during rotation of the disk and thus generates counting pulses or signals which are proportional to the volume of solution delivered by piston 45 to line 44. The pulse emitter or light source 47 is operationally connected to an analysis computer means 48 and that the generated counting pulses are fed into the computer 48. As is apparent, the amount of standardized $Cr^{+6}$-ion containing solution fed into analysis container 31 via burette means 43 is exactly proportional to the count signal supplied to the computer 48. Measurement electrodes 50 are positioned in container 31 in contact with the solution 40 therein and are connected to the analysis computer means 48 via lines 49 so that for each added volume of $Cr^{+6}$-ion containing solution to the solution 40 in container 31, a different current value is measured and an appropriate signal is sent to the computer 48. The computer means 48 integrates these signals so that a function $I=F(Q)$ is given for each measured current value. When the measured current value falls below a predetermined magnitude, the computer 48 immediately delivers a signal to the master process control means 51, which is operationally connected with the computer 48. The master process control means issues a command to the burette means 43 to shut-off titrating fluid to line 44. The biamperometric titration is now completed. However, it is now necessary to computationally determine the true end point of the titration, the so-called "neutral point." Such computations occur, as is described below, in computer means 48 which determines and indicates this neutral point, and thus the amount of organic materials or contaminants in the water sample under analysis, on a scale 52 of a data output means 53 operationally connected to the computer 48. All control commands are issued by the master process control means 51, which as is apparent, is operationally coupled to the various valve means, burette means, fluid-flow line, etc. in the overall system and to a suitable power source. Control means 51 may comprise any known command device, for example such as is available under the tradename "Siemens MC 210 E" or other like device which is capable of controlling pneumatically, hydraulically or electrically operated devices, such as valves, pumps, etc. in accordance with a predetermined program.

Referring now to FIG. 3, the analytical system of the invention includes two separate pneumatic control circuits which are connected via control lines 54 and 55 to a main source 56 of compressed gas. The source 56 is provided with a main line 56a having a control valve 56b feeding compressed gas into two reduction valves 57 and 58, each connected to valve 56b. The compressed gas source 56 has a compressed gas, such as air, at a fluid pressure at about 6 to 7 bar and the reducing valves 57 and 58 reduce this pressure to 5 bar for a first control line 54 and to 0.01 bar for a second control line 55. The control line 54 provides pressurized gas for controlling the pneumatically actuable piston burettes, syringes and valves whereas control line 55 provides pressurized gas for moving fluids in the various fluid-flow lines as well as in the various containers, for example, for moving the fluid mixture from collecting container 11 into the reactor container 20.

Sulfuric acid at a concentration of 25% (at source 33) or 98% (at source 23) is utilized in the various solutions requiring acid. The distilled water is utilized were required as a diluting agent.

FIG. 4 graphically illustrates the path of biamperometric titration of a diluted solution containing an excess amount of $Fe^{+2}$-ions with a standardized $Cr^{+6}$-ion containing solution. The amount of $Cr^{+6}$-ion solution added is indicated in ml. units along the abscissa and the current strength measured during each unit addition of titration solution is indicated in $\mu A$ units along the ordinate. As can be seen, the resultant curve M approximately corresponds to a hyperbolic function. During a titration, as soon as the measured current strength decreases to a pre-selected value, in the exemplary embodiment, to 2.0 $\mu A$, at the addition of each 0.2 ml. unit of titration solution thereafter, the individual measurement current valves, M1, M2 ..., etc, are fed into the computer 48, which as was earlier described, terminates the titration process upon attainment of a pre-selected threshold current valve, in the exemplary embodiment, 0.5 $\mu A$, corresponding to point Mn on the illustrated curve M. On the basis of the approximated curve function, the computer, by extrapolation, determines the point of intersection of curve M with the abscissa, i.e., determine the neutral point AP.

The determination of the amount Q (in mg/l) of organic materials, in the water sample is then computationally attained by the computer 48 in accordance with the following equation:

$$Q = (1 - \frac{a}{b}) \cdot \frac{Vc \cdot n^* \cdot o}{2} \cdot \frac{1000}{V}$$

wherein:
a is the residual amount of $Cr^{+6}$-ions after the oxidation-reduction reaction between the water sample and the reagent solutions (in $\mu Eg$);
b is a compensation value based on the purity (from organic contaminants) of the chemicals used, as well as from "blank" reaction of the $Cr^{+6}$-ion containing solution with the distilled water (in $\mu Eg$);
Vc is the volume of potassium dichromate solution added to the water sample (in the exemplary embodiment, 2.5 ml.);
n* is the normality of the standardized potassuim dichromate solution;
V is the volume of the water sample (in the exemplary embodiment, 5 ml.); and
<o> is the atomic weight of oxygen.

In order to determine the value of (a/b) in the above equation and if nc is the normality of the standardized titration solution utilized in the biamperometric titration, one utilizes the relation:

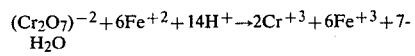

wherein:
AFe is the amount of reduced $Fe^{+2}$-ions in the solution being titrated;
Vep is the amount of consumed potassuin dichromate solution, in ml., during titration of the water sample; and
Vco is the amount of consumed potassuim dichromate solution, in ml., during titration of the blank reaction.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalence may be restored to, falling within the scope of the invention as claimed.

What we claim as our invention:
1. In a process for determining the amount of the dispersed water-immiscible solid organic materials in sewage water whereby a calculated amount of sulfuric acid and silver sulfate are added to a defined amount of sewage water and admixed therewith to obtain an analysis sample; an amount of $K_2Cr_2O_7$-solution is admixed with such analysis sample to obtain a reaction sample; said reaction sample is heated substantially up to the boiling point thereof and maintained at the resultant temperature for a period of time until substantially all of the oxygen, released from the $K_2Cr_2O_7$-solution during the reduction of $Cr^{+6}$-ions into $Cr^{+3}$-ions, reacts with and oxidizes the organic materials in such reaction sample; and a residual amount of $Cr^{+6}$-ions within the resultant reaction sample is determined by titrating such sample with a $Fe^{+2}$-ion containing solution so that a reaction in accordance with the following formula occurs:

$$(Cr_2O_7)^{-2} + 6Fe^{+2} + 14H^+ \rightarrow 2Cr^{+3} + 6Fe^{+3} + 7H_2O$$

wherein the consumed amount of the $Fe^{+2}$-ion containing solution as measured by titration, comprises an indirect indication of the amount of organic materials in the defined amount of sewage water, the improvement comprising:
generating a required amount of $Fe^{+2}$-ions for said titration via a coulometric reduction in an $Fe^{+3}$-ion containing solution during the preparation and reaction of said reaction sample.

2. In a process as defined in claim 1 wherein the amount of $Fe^{+2}$-ions generated in the $Fe^{+3}$-ion containing solution is in excess of the expected amount of residual $Cr^{+6}$-ions in the resultant reaction sample, thereafter mixing such resultant reaction sample with the $Fe^{+2}$-ion containing solution in such a manner that substantially all $Cr^{+6}$-ions are reduced to $Cr^{+3}$-ions, and then determining the residual amount of $Fe^{+2}$-ions in the resultant mixture by means of biamperometric titration with a $Cr^{+6}$-ion containing solution.

3. In a process as defined in claim 2 wherein biamperometric titration comprises supplying a measured current value at constant time intervals from the titrated mixture to a computer means so that when such measured current value falls below a preselected threshold value, said computer means terminates the titration process and extrapolates and displays the neutral point of titration.

4. An automated analysis process for analyzing the amount of dispersed water-immiscible solid organic substances in sewage water comprising, in combination, (a) obtaining a precise sample of sewage from a sewage source;

(b) admixing select reagent solutions, including a $K_2Cr_2O_7$-solution with said sewage sample under controlled heat-time conditions so that a reaction occurs between the sewage and the reagents and substantially all of the organic materials in said sample are oxidized while simultaneously at least some $Cr^{+6}$-ions are reduced to $Cr^{+3}$-ions, while substantially simultaneously, at a location remote from said reaction, generating a precise amount of $Fe^{+2}$-ions in an $Fe^{+3}$-ion containing solution via a coulometric reduction process;

(c) admixing the reacted sewage-reagent solution with the so-generated $Fe^{+2}$-$Fe^{+3}$-ion containing solution so that any residual $Cr^{+6}$-ions in the sewage-reagent solution are reduced to $Cr^{+3}$-ions and at least some $Fe^{+2}$-ions remain;

(d) biamperometrically titrating the resultant $Fe^{+2}$-ion containing solution with a standardized $Cr^{+6}$-ion containing solution to an end point; and (e) computationally determining the precise amount of $Fe^{+2}$-ions within the titrated solution and converting the same into an indication of the amount of organic materials within the sewage sample.

* * * * *